United States Patent [19]

Shinoda et al.

[11] Patent Number: 5,668,120
[45] Date of Patent: Sep. 16, 1997

[54] IONTOPHORETIC DELIVERY OF BISPHOSPHONATES TO THE ALVEOLAR BONE

[75] Inventors: Hisashi Shinoda; Hiroshi Horiuchi, both of Sendai, Japan

[73] Assignee: The Procter & Gamble Company, Cincinnati, Ohio

[21] Appl. No.: 495,266

[22] Filed: Jun. 27, 1995

Related U.S. Application Data

[63] Continuation of Ser. No. 228,982, Apr. 18, 1994.
[51] Int. Cl.⁶ .................................................. A61K 31/66
[52] U.S. Cl. ...................... 514/102; 514/103; 514/108
[58] Field of Search ............................... 514/102, 108, 514/103

[56] References Cited

U.S. PATENT DOCUMENTS

| | | | |
|---|---|---|---|
| 4,153,060 | 5/1979 | Korostoff et al. | 128/419 |
| 4,979,938 | 12/1990 | Stephen et al. | 604/20 |
| 5,270,365 | 12/1993 | Gertz et al. | 514/108 |
| 5,283,057 | 2/1994 | Shinoda | 424/54 |

FOREIGN PATENT DOCUMENTS

| | | | |
|---|---|---|---|
| 448 299 | 9/1991 | European Pat. Off. | |
| 552 878 | 7/1993 | European Pat. Off. | |
| 600834A1 | 6/1994 | European Pat. Off. | A61K 31/66 |

OTHER PUBLICATIONS

Singh, P. and Maibach, H.I. "Iontophoresis in Drug Delivery: Basic Principles and Applications", *Critical Reviews in Therapeutic Drug Carrier Systems*, vol. 11 (1994), pp. 161–213.

Kasting, G. B., E. W. Merritt and J. C. Keister, "An In Vitro Method for Studying the Iontophoretic Enhancement of Drug Transport Through Skin", *Journal of Membrane Science*, vol. 35 (1988), pp. 137–159.

Slough, C. L., M. J. Spinelli and G. B. Kasting, "Transdermal Delivery of Etidronate (EHDP) in the Pig Via Iontophroesis", *Journal of Membrane Science*, vol. 35 (1988), pp. 161–165.

*Primary Examiner*—Theodore J. Criares
*Attorney, Agent, or Firm*—Betty J. Zea; Karen F. Clark; David L. Suter

[57] ABSTRACT

The present invention relates to methods of inhibiting alveolar bone resorption or the undesirable movement of teeth of a human or other animal comprising:

a) administering a reservoir to the gingival tissue of the oral cavity such that the reservoir is in contact with the exposed tissue nearest to the alveolar bone to be treated wherein the reservoir is a composition having a pH which maintains an active compound in a negatively charged state and comprises a safe and effective amount of the active compound having the structure:

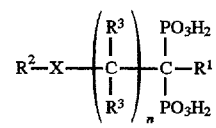

wherein: n is an integer from 0 to 7 (preferably from 0 to 3, more preferably 1); $R^1$ is hydrogen, chloro, amino, or hydroxy (preferably hydrogen or hydroxy); X is —NH—, quaternary amine, oxygen, sulfur, or a single bond (preferably —NH— or single bond); $R^2$ is a 5- to 7-membered carbocycle (preferably 6- to 7-membered, more preferably benzene or cycloheptyl), a 5- to 7-membered heterocycle having from 1 to 3 heteroatoms (preferably a 6-membered heterocycle having 1 or 2 nitrogen atoms, wherein a ring nitrogen may be quaternarized), —NH₂, amino substituted with one alkyl or two alkyl (preferably $C_1$–$C_5$) groups to give a secondary or tertiary amine, respectively, quaternary amino, or hydrogen; wherein if $R^2$ is a substituted 5- to 7-membered carbocycle or heterocycle, the substituent is one or more substituents selected from the group consisting of substituted and unsubstituted, saturated or unsaturated alkyl having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof; each $R^3$ is, independently, hydrogen, or substituted or unsubstituted alkyl (saturated or unsaturated) having from 1 to about 4 carbon atoms; or their pharmaceutically-acceptable salts and esters; and b) passing a safe and effective amount of electrical current through two electrodes, one electrode being a negative electrode in contact with the reservoir, the second electrode being a positive electrode in contact with the human or other animal being treated.

19 Claims, No Drawings

IONTOPHORETIC DELIVERY OF BISPHOSPHONATES TO THE ALVEOLAR BONE

This is a continuation of application Ser. No. 08/228 982, filed on Apr. 18, 1994.

BACKGROUND OF THE INVENTION

Certain geminal bisphosphonic acid compounds, including their salts and esters, are effective against alveolar bone loss and unwanted tooth movement. Problems with such compounds include that the compounds are generally negatively charged molecules and not capable of penetrating oral tissue very readily. Although such drugs have been administered systemically, their rate of absorption is quite poor.

Iontophoresis is a technique for delivering ions into a person's tissue by placing a solution, or other medium containing the ion, in contact or close proximity with the tissue; the solution or medium containing the ions is typically carried by a first electrode pouch or receptacle. A second or dispersive electrode is placed against the tissue within some proximity of the first electrode. Ions are caused to migrate from the ion-carrying medium through the tissue by the application of an electrical potential or voltage of the appropriate polarity to the two electrodes. A controlled current is established by providing a sufficient voltage differential between the first and second electrodes, and placing a limiting resistance or other current-limiting device elsewhere in the circuit.

Applicant has surprisingly found that when administered via iontophoresis, certain bisphosphonate compounds not only inhibit alveolar bone resorption associated with periodontal disease and stabilize tooth movement during orthodontic procedures, but they do so at low dosages. When administered via iontophoresis, the dosage amount may be low enough such that there is little or no systemic level of drug, but the dosage is nonetheless effective in providing a local benefit.

SUMMARY OF THE INVENTION

The present invention relates to methods of inhibiting alveolar bone resorption or the undesirable movement of teeth of a human or other animal comprising:

a) administering a reservoir to the gingival tissue of the oral cavity such that the reservoir is in contact with the exposed tissue nearest to the alveolar bone to be treated wherein the reservoir is a composition having a pH which maintains an active compound in a negatively charged state and comprises a safe and effective amount of the active compound having the structure:

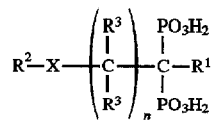

wherein: n is an integer from 0 to 7 (preferably from 0 to 3, more preferably 1); $R^1$ is hydrogen, chloro, amino, or hydroxy (preferably hydrogen or hydroxy); X is —NH—, quaternary amine, oxygen, sulfur, or a single bond (preferably —NH— or single bond); $R^2$ is a 5- to 7-membered carbocycle (preferably 6- to 7- membered, more preferably benzene or cycloheptyl), a 5- to 7-membered heterocycle having from 1 to 3 heteroatoms (preferably a 6-membered heterocycle having 1 or 2 nitrogen atoms, wherein a ring nitrogen may be quaternarized), —$NH_2$, amino substituted with one alkyl or two alkyl (preferably $C_1$–$C_5$) groups to give a secondary or tertiary amine, respectively, quaternary amino, or hydrogen; wherein if $R^2$ is a substituted 5- to 7-membered carbocycle or heterocycle, the substituent is one or more substituents selected from the group consisting of hydrogen, substituted and unsubstituted, saturated or unsaturated alkyl having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof; each $R^3$ is, independently, hydrogen, or substituted or unsubstituted alkyl (saturated or unsaturated) having from 1 to about 4 carbon atoms; or their pharmaceutically-acceptable salts and esters; and b) passing a safe and effective amount of electrical current through two electrodes, one electrode being a negative electrode in contact with the reservoir, the second electrode being a positive electrode in contact with the human or other animal being treated.

DETAILED DESCRIPTION OF THE INVENTION

The essential as well as non-essential aspects of this invention are described in the following paragraphs.

Bisphosphonic Acid

This invention relates to iontophoretic delivery to the oral tissue of a safe and effective amount of geminal bisphosphonic acid compounds ("BPs"), or their pharmaceutically-acceptable salts and esters.

Particularly preferred bisphosphonates useful herein are of the formula:

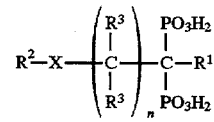

wherein: n is an integer from 0 to 7 (preferably from 0 to 3, more preferably 1); $R^1$ is hydrogen, chloro, amino, or hydroxy (preferably hydrogen or hydroxy); X is —NH—, quaternary amine, oxygen, sulfur, or a single bond (preferably —NH— or single bond); $R^2$ and is a subsituted or unsubstituted 5- to 7-membered carbocycle (preferably 6- to 7- membered, more preferably benzene or cycloheptyl), a subsituted or unsubstituted 5- to 7-membered heterocycle having from 1 to 3 heteroatoms (preferably a 6-membered heterocycle having 1 or 2 nitrogen atoms, wherein a ring nitrogen may be quaternarized), —$NH_2$, amino substituted with one alkyl or two alkyl (preferably $C_1$–$C_5$) groups to give a secondary or tertiary amine, respectively, quaternary amino, or hydrogen; wherein if $R^2$ is a substituted 5- to 7-membered carbocycle or heterocycle, the substituent is one or more substituents selected from the group consisting of substituted and unsubstituted, saturated or unsaturated alkyl having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof, hydrogen being preferred; each $R^3$ is, independently, hydrogen, or substituted or unsubstituted alkyl (saturated or unsaturated) having from 1 to about 4 carbon atoms, pref; and their pharmaceutically-acceptable salts and esters.

The term "pharmaceutically-acceptable salts and esters", as used herein, means hydrolyzable esters and salts of the bone-active phosphonates which have the same general pharmacological properties as the acid form from which they are derived, and which are pharmaceutically acceptable. Pharmaceutically-acceptable salts include, for example, alkali metals (e.g., sodium and potassium), alkaline earth metals (e.g., calcium and magnesium), non-toxic heavy metals (e.g., stannous and indium), and ammonium and low molecular weight substituted ammonium (e.g., mono-, di- and triethanolamine) salts. Preferred compounds are the sodium, potassium, and ammonium salts. Pharmaceutically-acceptable esters include unsubstituted and substituted alkyl, aryl and phosphoryl esters. Nonlimiting examples of pharmaceutically-acceptable esters include, for example, isopropyl, tertiarybutyl, 2-chloroethyl, 2,2,2-trichloroethyl, 2,2,2-trifluoroethyl, p-toluenesulfonylethyl, glycyl, sarcosyl, benzyl, phenyl, 1,2-hexanoylglyceryl, p-nitrophenyl, 2,2 dimethyl-1,3-dioxolene-4-methyl, isopentenyl, o-carbomethoxyphenyl, piraloyloxymethylsalicylyl, diethylamidophosphoryl, pivaloyloxymethyl, acyloxymethyl, propionyloxymethyl, isobutyryloxymethyl, dodecyl, octadecyl, and isopropyloxymethyl.

Specific examples and definitions for substituents useful in the bisphosphonates are described in European Patent Publication 298,553, Ebetino, published Jan. 11, 1989 (incorporated by reference herein). Bisphosphonates useful in the methods of this invention, and methods for making such compounds, are described in the following patent documents, all incorporated by reference herein: U.S. Pat. No. 3,553,314, Francis, issued Jan. 5, 1971; U.S. Pat. No. 3,683,080, Francis, issued Aug. 8, 1972; U.S. Pat. No. 3,846,420, Wollmann et al., issued Nov. 5, 1974; U.S. Pat. No. 3,899,496, Schindler et al., issued Aug. 12, 1975; U.S. Pat. No. 3,941,772, Ploger et al., issued Mar. 2, 1976; U.S. Pat. No. 3,957,160, Ploger et al., issued May 18, 1976; U.S. Pat. No. 3,962,432, Schmidt-Dunker, issued Jun. 8, 1976; U.S. Pat. No. 3,979,385, Wollmann et al., issued Sep. 7, 1976; U.S. Pat. No. 3,988,443, Ploger et al., issued Oct. 26, 1976; U.S. Pat. No. 4,054,598, Blum et al., issued Oct. 18, 1977; U.S. Pat. No. 4,113,861, Fleisch et al., issued Sep. 12, 1978; U.S. Pat. No. 4,117,090, Ploger, issued Sep. 26, 1978; U.S. Pat. No. 4,134,969, Schmidt-Dunker, issued Jan. 16, 1979; U.S. Pat. No. 4,267,108, Blum et al., issued May 12, 1981; U.S. Pat. No. 4,304,734, Jary et al., issued Dec. 8, 1981; U.S. Pat. No. 4,330,537, Francis, issued May 18, 1982; U.S. Pat. No. 4,407,761, Blum et al., issued Oct. 4, 1983; U.S. Pat. No. 4,469,686, Andrews, issued Sep. 4, 1984; U.S. Pat. No. 4,578,376, Rosini, issued Mar. 25, 1986; U.S. Pat. No. 4,608,368, Blum et al., issued Aug. 26, 1986; U.S. Pat. No. 4,621,077, Rosini et al., issued Nov. 4, 1986; U.S. Pat. No. 4,687,767, Bosies et al., issued Aug. 18, 1987; U.S. Pat. No. 4,687,768, Benedict et al., issued Oct. 18, 1987; U.S. Pat. No. 4,711,880, Stahl et al., issued Dec. 8, 1987; U.S. Pat. No. 4,719,203, Bosies et al., issued Jan. 12, 1988; U.S. Pat. No. 4,927,814, Gall et al., issued May 22, 1990; U.S. Pat. No. 4,990,503, Isomura et al., issued Feb. 5, 1991; U.S. Pat. No. No. 5,019,651, Kieczykowski, issued May 28, 1991, German Offenlegungsschrift 2, 104,476, Worms, published Aug. 17, 1972; German Offenlegungsschrift 2,343,147, Ploeger et al., published Apr. 3, 1975; German Offenlegungsschrift 2,360,798, Worms et al., published Jun. 26, 1975; German Offenlegungsschrift 2,513, 966, Schmidt-Dunker, published Oct. 7, 1976; German Offenlegungsschrift 2,541,981, Eimers et al., published Mar. 24, 1977; German Offenlegungsschrift 3,334,211, Blum, published Apr. 4, 1985, Japanese Patent Publication 78/59, 674, Suzuki et al., published May29, 1978; Japanese Patent Publication 79/135,724, Suzuki et al., published Oct. 22, 1979; Japanese Patent Publication 80/98193, Suzuki et al., published Jul. 25, 1980; European Patent Publication 88,359, Blum et al., published Sep. 14, 1983; European Patent Publication 100,718, Breliere et al., published Feb. 15, 1984; European Patent Publication 186,405, Benedict et al., published Jul. 2, 1986; European Patent Publication 97,478, Bosies et al., published Oct. 15, 1986; European Patent Publication 230,068, Benedict et al., published Jul. 29, 1987; European Patent Publication 273,514, Ebetino et al., published Jul. 6, 1988; European Patent Publication 274,158, Ebetino et al., published Jul. 13, 1988; European Patent Publication 282,309, Sakamoto et al., published Sept. 14, 1988; European Patent Publication 282,320, Isomura et al., published Sep. 14, 1988; PCT Patent Publication 87/03598, Binderup et al., published Jun. 18, 1987; and PCT Patent Publication 88/00590, Gall et al., published Jan. 28, 1988.

Preferred bone-active phosphonates useful in the methods of this invention include: referred bone-active phosphonates useful in the methods of this invention include: 1-hydroxyethane-1,1-bisphosphonic acid; dichloromethane bisphosphonic acid; 3-amino-1-hydroxypropane-1,1-bisphosphonic acid; 6-amino-1-hydroxyhexane-1,1-bisphosphonic acid; 4-amino-1-hydroxybutane-1,1-bisphosphonic acid; 2-(3-pyridyl)-1-hydroxyethane-1,1-bisphosphonic acid; 2-(N-imidazoyl)-1-hydroxyethane-1,1-bisphosphonic acid; 3-(N-pentyl-N-methylamino)-1-hydroxypropane-1,1-bisphosphonic acid; 3-(N-pyrollidino)-1-hydroxypropane-1,1-bisphosphonic acid; N-cycloheptylaminomethanebisphosphonic acid; S-(p-chlorophenyl) thiomethane-bisphosphonic acid; 4-amino-1-hydroxybutylidene-1,1-bisphosphonic acid; (7-dihydro-1-pyrindine)methane bisphosphonic acid; (7-dihydro-1-pyrindine)hydroxymethane bisphosphonic acid; (6-dihydro-2-pyrindine)hydroxy-methanebisphosphonic acid; 2-(6-pyrolopyridine)-1-hydroxyethane-1,1-bisphosphonic acid; and pharmaceutically-acceptable salts and esters thereof.

Particularly preferred bone-active phosphonates useful in the methods of this invention include: 4-amino-1-hydroxybutane-1,1-bisphosphonic acid; 2-(3-pyridyl)-1-hydroxyethane-1,1-bisphosphonic acid; 3-(N-pentyl-N-methylamino)-1-hydroxypropane-1,1-bisphosphonic acid; N-cycloheptylaminomethanebisphosphonic acid; S-(p-chlorophenyl) thiomethane-bisphosphonic acid; (7-dihydro-1-pyrindine)methane bisphosphonic acid; and pharmaceutically-acceptable salts and esters thereof.

The aminoethane bisphosphonic acid compounds, however, are best prepared as follows:

The Risedronate Active Ingredient

The term "risedronate", as used herein, denotes the bisphosphonate compound 3-pyridyl-1-hydroxyethylidene-1,1-bisphosphonic acid and has the following structure:

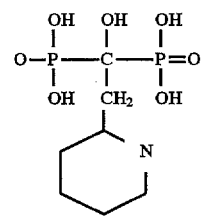

The compound risedronate is further described in the following publication, all hereby incorporated by reference herein: EPO Patent Application 0,186,405 of Benedict et al., assigned to The Procter & Gamble Co., published Jul. 2, 1986; and "An International Conference, Bisphosphonates: Current Status and Future Prospects, The Royal college of Physicians, London, England, May 21–22, 1990, organized by IBC Technical Services.

The term "risedronate active ingredient" includes risedronate, risedronate salts, and risedronate esters, or any mixture thereof. Any pharmaceutically-acceptable, non-toxic salt or ester of risedronate may be used as the risedronate active ingredient in the oral dosage forms useful for the present invention. The salts of risedronate may be acid addition salts, in particular the hydrochloride, but any pharmaceutically-acceptable, non-toxic organic or inorganic acid salt may be used. In addition, salts formed with the carboxylic acid group may be used, including, but not limited to, alkali metal salts (K, Na) and alkaline earth metal salts (Ca, Mg), the Ca- and Na- salts being preferred.

Particularly, other esters of risedronate which are suitable for use as the active ingredient in the invention disclosed herein are straight chain or branched chain $C_1$–$C_{18}$ alkyl esters, including, but not limited to, methyl, ethyl, propyl, isopropyl, butyl, isobutyl, amyl, hexyl, heptyl, octyl, nonyl, decyl, lauryl, myristyl, cetyl, and stearyl; straight chain or branched $C_2$–$C_{18}$ alkenyl esters, including, but not limited to, vinyl, alkyl, undecenyl, and linolenyl; $C_3$–$C_8$ cycloalkyl esters, including, but not limited to, vinyl, alkyl, undecenyl, and linolenyl; $C_3$–$C_8$ cycloalkyl esters, including, but not limited to, cyclopropyl, cyclobutyl, cyclopentyl, cyclohexyl, cycloheptyl, and cyclooctyl; aryl esters, including, but not limited to, phenyl, toluyl, xylyl, and naphthyl; alicyclic esters, including, but not limited to methyl; and aralkyl esters, including, but not limited to, benzyl, and phenethyl.

Generally speaking, the proper selection of the risedronate active ingredient depends on the selected type of formulation. The physical and chemical characteristics of the active ingredient must be taken into account when selecting suitable pharmaceutically-acceptable excipients for use in the dosage forms containing the risedronate active ingredient.

Synthesis of N-(2-(3-picolyl))aminoethane BP

The above-named compound is prepared via a typical Michael reaction between tetraethyl vinylbisphosphonate and 2-amino-3-picoline. (See H. O. House, *Modern Synthetic Reaction* 2nd Ed. W. A. Benjamin Inc. p. 595–623, the disclosure of which is incorporated herein by reference.)

To a solution of 1.62 g (15 mmol) of 2-amino-3-picoline in tetrahydrofuran at 5° C. is added 4.50 g (15 mmol) tetraethyl vinylbisphosphonate. The reaction mixture is stirred at room temperature for 16 hours. Evaporation of the solvent and chromatography (acetone/hexane, 4/1) of the product on silica gel give pure tetraethyl N-(2-(3-picolyl))-2-aminoethane bisphosphonate. P-31 NMR of the pure tetraethyl ester in $CDCl_3$ shows a resonance at 22.1 ppm. The ester is hydrolyzed in refluxing 6N HCl overnight. The product showed a P-31 NMR signal in $D_2O$ at pH=12 of 19.0 ppm.

N-(2-pyridyl)-2-aminoethane BP and N-(2-(5-picolyl))-2-aminoethane BP are prepared in an identical manner.

Compounds having the general formula:

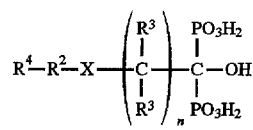

(wherein n is an integer of from 1 to about 5, preferably n=1; and X, $R^2$ and $R^3$ are as described hereinbefore, with preferred $R^2$ being pyrimidine and especially pyridine, preferred $R^4$ being one or more substituents selected from the group consisting of hydrogen, methyl, amino, chloro, nitro, methoxy, hydroxy, and combinations thereof, preferred X being a single bond, and preferred $R_3$ being hydrogen) are best prepared as follows:

Synthesis of 2-(2-pyridyl)-1-hydroxy-ethane-1,1-bisphosphonic acid:

A 3-neck round-bottom flask fitted with a reflux condenser and a magnetic stir bar is charged with 6.94 grams (0.04 mole) 2-pyridine acetic acid, 9.84 grams (0.14 mole) phosphorus acid, and 150 ml of chlorobenzene. This reaction mixture is heated on a boiling water bath, and 16.5 grams (0.12 mole) phosphorus trichloride is added dropwise with stirring. This reaction mixture is heated for 2½ hours during which time a viscous yellow oil forms. The reaction mixture is then cooled in an ice bath and the chlorobenzene solution is decanted off from the solidified product. The reaction flask containing this solidified product is charged with 150 ml of water and heated in a boiling water bath for several hours. The hot solution is then filtered through Celite 545®. 300 ml of methanol is added to the warm filtrate solution, and precipitate develops. After cooling in ice for 1 hour, the precipitate is filtered off and then washed with methanol/water (1/1 volume/volume), methanol, and ether, and air dried. The product may be recrystallised from hot water. The sample is characterized by P-31 and C-13 NMR.

In this invention the effective amount of active agent means that amount needed to produce the intended result following its iontophoretic administration. The effective amount will vary, depending, among other factors, on the physiological effect as determined by the tissue level of desired active agent, rate of clearance of active agent, and intradermal metabolism desired.

The amount of active agent per administration and incorporated into a carrier for iontophoretic delivery should be from about 0.002 mg to about 20 mg preferably from about 0.01 mg to about 10 mg more preferably from about 0.1 mg to about 5 mg of the active agent.

Iontophoresis

During iontophoresis, charged compounds pass from a reservoir attached to the oral tissue of a person or animal into the tissue therebeneath. The process is one wherein the rate of delivery is a function of current, active agent concentration, and presence of other ions. It is a generally held belief that higher concentration of compound, higher levels of current, and lower concentration of their ions will result in delivery of a greater amount of compound.

Appropriate voltage should be utilized sufficient to deliver a safe and effective amount of electrical current. By "safe and effective amount" as used herein is meant an amount of current sufficient to induce a significant positive modification in the condition to be treated, but low enough to avoid serious side effects (at a reasonable benefit/risk ratio), within the scope of sound medical judgment. The safe and effective amount of the current may vary with the particular condition being treated, the age and physical condition of the patient being treated, the severity of the condition, the duration of the treatment, the nature of concurrent therapy, the specific compound or composition employed, the particular pharmaceutically-acceptable carrier utilized, and like factors. An voltage delivering an electrical current of from about 0.01 to about 5.0 ma/cm$^2$; preferably from about 0.1 to about 1 ma/cm$^2$; also more preferably from about 1 to about 4.5 ma/cm$^2$ should be sufficient. High voltage electroporation as described in U.S. Pat No. 5,019,034, issued May 28, 1991 to Weaver et. al, and incorporated herein by reference may also be used.

The methods and compositions of the present invention are particularly advantageous compared to prior methods and compositions. Prior methods and compositions typically relied on tissue damaging or tissue altering compositions such as permeation enhancers. Unlike tissue permeation enhancers that alter the gingival epithelium, the compositions and methods of the present invention are not directed toward altering the gingival epithelium and yet achieve an enhanced tissue concentration with iontophoretic delivered active agents.

The following terms are defined as used in this document. "Ion" refers to an atom or radical that has lost or gained one or more electrons to acquire an electric charge. "Active agent" refers to the entity chosen to be delivered by iontophoresis. Thus, active agent refers to the chosen entity and the ionic form of the chosen entity for delivery, such as halide salts of a chosen entity to be delivered (e.g., risedronate and an ionic form of risedronate for delivery such as calcium risedronate). "Patient" refers to animals, including humans, household animals such as dogs and cats, livestock such as cattle, horses, sheep, pigs, goats and rabbits, laboratory animals such as mice and rats, and zoo animals such as exotic species.

The methods and compositions of the invention are not limited to practice with any one particular iontophoretic system. Generally, iontophoretic devices comprise at least two electrodes, an electrical energy source (e.g., a battery) and at least one reservoir which contains an active agent to be delivered. Several iontophoretic devices are known, such as those disclosed in P. Tyle, *Pharmaceutical Research* 3:318 (1986).

The active agent must be maintained in the donor compartment in a chemically pure form. Electrochemical reaction of the active at the electrode are to be avoided. When iontophoresis of an active agent is performed, the compound passes through the gingival epithelium, through the intervening oral tissue and into the alveolar bone. In a situation wherein the gingival epithelium is the rate-limiting barrier, the blood flow in the vasculature is of little consequence. When the rate of delivery of the active agent is enhanced over passive delivery, as in the case of iontophoresis, to the point where the ability of the vasculature to remove the compound is rate-limiting, then the blood flow in the vasculature becomes significant. Iontophoresis of a vasoconstrictor with an active agent, therefore enhances the tissue concentration of iontophoretically delivered active agents.

The ability to maintain proper concentration ratios of active agent to vasoconstrictor will depend upon the iontophoretic properties of the active agent and vasoconstrictor, and hence the relative proportions of the vasoconstrictor combined with the active agent.

Carrier

The term "pharmaceutically-acceptable composition" refers to the addition of salts, mold complexes, solid and liquid carriers, ionic forms, and the like, which do not significantly or adversely affect the properties of the active agent or its stability to be iontophoretically delivered. Pharmaceutically-acceptable compositions can be prepared by reference to general texts in the field, such as *Remington's Pharmaceutical Sciences*, Ed. A. F. Gennaro, 17th ed., 1985, Mack Publishing Co., Easton, Pa.

The pharmaceutically-acceptable composition, or reservoir, that contains the active agent to be delivered can be in the form of any material suitable for making contact between the iontophoresis unit and the oral tissue. Suitable materials include, but are not limited to, solutions, foams, gels, creams, and lotions; nonionic gel is preferred.

Iontophoresis solutions can comprise a liquid vehicle such as water, alcohol, propylene glycol, polyethylene glycol, or a mixture thereof. Such a vehicle may comprise from about 70% to about 99%, preferably from about 80% to about 98% of the solution.

Provided they are compatible with the vehicle components, optional agents may be added. Such agents can include surface active agents, such as poloxamer, sodium lauryl sulfate, and like; preservatives, such as methyl paraben, cetyl pyridinum chloride; flavoring agents, and coloring agents.

Iontophoresis gels can comprise a liquid or solution composition such as that described above, gelled with a suitable gelling agent. Such suitable gelling agents may include hydroxy propyl methyl cellulose, carboxy vinyl copolymer (Carbopol), food starch such as corn starch and potato starch, gums such as xanthan, karaya, alginic acid, biopolymers like chitosan, other polysaccharide gels, or similar hydrophilic aqueous gels capable of carrying ions. Specific examples of such gels include polyvinyl alcohol, polymethyl pyrrolidine, polyvinyl pyrrolidone, methyl cellulose, polyacrylamide, polyhemas, polyhema derivatives, food starch such as corn and potato starches and the like. The matrix selected should be nonirritating to a person's tissue, the matrix should have suitable viscosity and surfactant properties to obtain good electrical contact with the tissue, and the ability to act as a carrier medium for the bisphosphonate ions. The preferred matrix is starch. A gelling agent may constitute from about 0.1% to about 10% of the composition, preferably between 0.2 to 2%.

Optional components may be added. Such optional components can include preservative such as methyl paraben, flavors, and sweeteners such as sorbitol. For example, if higher amount alcohol is used as a vehicle, additional preservative may not be necessary.

If desired, an anhydrous gel can also be formulated, for example, by using propylene glycol as a vehicle, without any water, and gelling propylene glycol with a suitable cellulosic or other polymer.

Iontophoresis foaming paste can comprise a pharmaceutically acceptable foaming surface active agent such as sodium lauryl sulfate, is sodium dodecyl sulfate, poloxamer, and like. When sodium lauryl sulfate is used, its concentration can be from about 0.1% to about 5%, preferably from about 0.5% to about 2%. Higher concentration provides increased foaming; lower concentration provides lesser foaming. For a dentifrice formulation, a pharmaceutically-acceptable dental abrasive is added. Suitable dental abrasives include colloidal silicon dioxide and others such as those disclosed by Cooley et al. in U.S. Pat. No. 3,070,510, issued Dec. 25, 1962, incorporated herein by reference.

Optionally, an opacifier such as titanium dioxide can be added to make the formulation opaque. In its absence, the composition would be clear or translucent.

Iontophoresis lotions and creams can comprise a fatty or oily component, an aqueous component, and a surface active agent as an emulsifier. Suitable fatty components can include petrolatum, fatty alcohol, fatty acid, and the like. Suitable surface active agents may include sodium lauryl sulfate, sorbitan esters, polyoxyethylene and polyoxypropylene derivatives and copolymers, natural and synthetic gums, cellulosics, and like. The making of a suitable lotion or cream for use in this invention is well known to those familiar with the science and art of making emulsion products.

The pH must be maintained in a range that is physiologically acceptable and maintains the bisphosphonate in a negatively charged state, preferably from about pH 3 to about pH 9, more preferably from about 5 to about 8. For short duration treatments (e.g., 2-3 minutes), a wider range might be tolerated. A key to maintaining constant pH over a longer period (e.g. longer than about 5 minutes) is the use of non-polarizing electrodes rather than metal electrodes or a combination of a salt bridge and a large surfaced metal electrode. Such non-polarizing electrodes include Ag/AgCl, and calomel electrodes. Ion exchange membranes which separate the donor solution from the anode or cathode may also be employed for this purpose, especially for oxidatively sensitive actives.

Preferred compositions useful for purposes of this invention have a maximum osmolarity of less than or equal to about 150 mM; preferably the osmolarity is less than this amount. The maximum ionic concentration should be a maximum of about 150 mM, preferably less. Preferably the active agent ions comprise a minimum of 25% of the mobile ion concentration of such compositions.

Optional Ingredients

The active agent for use in the method of the invention can be delivered alone, or in combination with other substances. Other substances can include other permeation enhancers, buffers, bacteriostatics, stabilizers, antioxidants, other active agents and the like, anti-inflammatories, antihistamines, antibiotics. Preferably the active agent is for non-systemic delivery. Specific examples of antibiotics include clindamycin, streptomycin, vancomycin, tetracyclines, metronidazole and azithromycin. The composition is typically dissolved in a suitable carrier for iontophoretic delivery.

In all dose forms, especially solutions and gels, addition of ethanol (from 0.001% to about 40%) may increase skin permeability and enhance bisphosphonate delivery. Perfumes and/or flavoring agents could be added, especially if the treatment were to be applied in the oral cavity without a patch. A local anesthetic (e.g. lidocaine, benzocaine) might be included to numb the site of application. A composition comprising a local anesthetic should be applied to the gingival tissue and left for at least approximately 30 seconds before the iontophoretic current is applied. Additional optional ingredients include anti-inflammatory agents to relieve pain and inflammation. Anionic NSAIDs are preferred, including but not limited to, α-propionic acids (e.g. ibuprofen, ketoprofen, naproxen, flurbiprofen), ketorolac, indomethacin, and meclofenamic acid.

Method of Use

The compositions previously described can be applied directly to the oral tissue or in a patch. In the former case, the application site must subsequently be contacted with an electrode to initiate iontophoretic treatment. All dose forms must be electrically conductive. Preferred dose forms include conductive gels applied with or without a patch, and conductive solutions contained within a patch.

Iontophoretic treatment according to this invention can last for from about 1 minute to about 24 hours, preferably for from about 2 minutes to about 2 hours, more preferably for from about 3 minutes to about 30 minutes, more preferably still from about 5 minutes to about 10 minutes. The frequency of treatment should be from about once per three months to about 10 times per day, preferably from about once per week to about 4 times per day, more preferably from about one time per day to about 2 times per day. Preferably a minimum of two treatments are administered.

The treatment regimen for use in the present invention includes the consideration of a variety of factors, including the type, age, weight, sex, medical condition of the patient, severity of the condition and active agent to be delivered. An ordinarily skilled dentist or physician can readily determine and prescribe and administer the effective amount of the agent required to prevent or arrest the progress of the condition by employing relatively low doses at first and subsequently increase the dose until a maximum response is obtained.

The following examples illustrate the specific embodiments of the invention described herein. As would be apparent to skilled artisans, various changes and modifications are possible and are contemplated within the scope of the invention described.

EXAMPLE I

Solution:

|  | Percentage by Weight |
| --- | --- |
| Risedronate | 0.5 |
| Alcohol, 95% | 7.8 |
| Methyl paraben | 0.15 |
| Cetyl pyridinium chloride | 0.05 |
| Poloxamer 407 | 0.5 |
| Flavor and Sweetener | As Needed |
| Phosphate-Saline Buffer, 0.1 molar, pH 7.4 | to make 100 |

The solution comprising 50 mM risedronate is applied to the gingival margin of a periodontitis patient with progressive disease. An iontophoretic current of 0.2 milliamperes is applied for 10 minutes. The treatment is repeated one week later. The progression of alveolar bone resorption is arrested for three months as determined by radiographic evaluation.

EXAMPLE II

Gel:

The gel can be formulated using techniques well known in the oral care field.

|  | Percentage by weight |
| --- | --- |
| Etidronate disodium (EHDP) | 1 |
| Hydroxy Propyl Methyl Cellulose | 2 |
| Methyl Paraben | 0.17 |
| Propyl Paraben | 0.04 |
| Sodium chloride | 0.9 |
| Flavor and Sweetener | As needed |
| Deionised water | q.s. |

The gel comprising 20 mM of EHDP is applied into the periodontal pockets of a periodontitis patient and 0.5 milliamperes of iontophoretic current are applied for ten minutes on each of four occasions over a one month period. Subsequent clinical and radiological evaluation demonstrate that the progression of alveolar bone loss has been arrested.

EXAMPLE III

Gel:

The gel can be formulated using techniques well known in the oral care field.

|  | Percentage by Weight |
| --- | --- |
| Risedronate | 0.14 |
| Corn Starch | 39 |
| Flavor and Sweetener | as needed |
| Water | q.s. |

An animal having experimentally induced periodontitis is treated on a first day by application of 50 μl of the gel comprising 8 mM risedronate around the neck of the tooth nearest a site of alveolar bone resorption. A current of 0.1 mA is applied to the gel for 10 min. The treatment is repeated on the third day again on the fifth day. As determined by microradiographs taken three days after the last treatment, loss of bone mineral density is found to be prevented relative to an untreated control site in the animal's mouth.

EXAMPLE IV

Lotion:

The lotion can be formulated using techniques well known in the oral care field.

|  | Percentage by weight |
| --- | --- |
| Alendronate | 0.25 |
| Stearic acid | 7 |
| Methyl paraben | 0.15 |
| Propyl paraben | 0.05 |
| Xanthan gum | 0.7 |
| Sodium hydroxide, 5% solution | to pH 6.8 |
| Sodium hydroxide | 0.7 |
| Deionised water | q.s. |

Following orthodontic repositioning of a tooth, the lotion comprising 80 mM of alendronate is applied to the gingival margin of that tooth and an iontophoretic current of 1 milliampere is applied for five minutes on two occasions, three weeks apart. Subsequent clinical evaluation demonstrates that the tooth is stable and there is no indication of tooth movement back toward its prior position.

EXAMPLE V

Foaming Paste:

The paste can be formulated using techniques well known in the oral care field.

|  |  |
| --- | --- |
| Risedronate | 1 |
| Colloidal silicon dioxide | 5 |
| Titanium dioxide | 0.25 |
| Carbopol 934 | 0.3 |
| Sodium lauryl sulfate | 1.5 |
| Sodium hydroxide, 5% solution | to pH 5.5 |
| Methyl paraben | 0.15 |
| Propyl paraben | 0.05 |
| Flavor and Sweetener | as desired |
| Deionised water | q.s. |

During one year of orthodontic treatment the anchor teeth of a patient are treated every other month by application to the gingival margin of the foaming paste comprising 10 mM risedronate in conjunction with 15 minutes of a 0.1 milliamperes iontophoretic current. This treatment leads to stable re-positioning of the desired teeth within 12 months without changing the position or stability of the anchor teeth.

What is claimed is:

1. A method of inhibiting alveolar bone resorption or stabilize tooth movement during orthodontic procedures of a human or other animal comprising:

a) administering a reservoir to the gingival tissue of the oral cavity such that the reservoir is in contact with the exposed tissue nearest to the alveolar bone to be treated wherein the reservoir is a composition having a pH which maintains an active compound in a negatively charged state and comprises from about 0.002 mg to about 20 mg of the active compound having the structure:

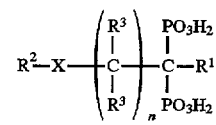

wherein: n is an integer from 0 to 7; $R^1$ is hydrogen, chloro, amino, or hydroxy; X is —NH—, quaternary amine, oxygen, sulfur, or a single bond; $R^2$ is a 5- to 7-membered carbocycle, a 5- to 7-membered heterocycle having from 1 to 3 heteroatoms, —$NH_2$, amino substituted with one alkyl or two alkyl groups to give a secondary or tertiary amine, respectively, quaternary amino, or hydrogen; wherein if $R^2$ is a substituted 5- to 7-membered carbocycle or heterocycle, the substituent is one or more substituents selected from the group consisting of substituted and unsubstituted, saturated or unsaturated alkyl having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, or combinations thereof; each $R^3$ is, independently, hydrogen, or substituted or unsubstituted alkyl saturated or unsaturated having from 1 to about 4 carbon atoms; or their pharmaceutically-acceptable salts and esters; and b) passing a safe and effective amount of electrical current through two electrodes, one electrode being a negative electrode in contact with the reservoir, the second electrode being a positive electrode in contact with the human or other animal being treated;

wherein the composition has a maximum osmolarity of about 150 mM and the electrical current is passed from about 1 minute to about 24 hours and wherein the negatively charged active compound passes from the reservoir in contact with the tissue into the tissue therebeneath.

2. The method according to claim 1 wherein the reservoir is an oral composition comprising from about 0.002 mg to about 10 mg of the active compound wherein: X is a single bond; $R^2$ is selected from the group consisting of quaternary amine, pyridine, pyridazine, pyrimidine and pyrazine; n is an integer from 0 to about 5; $R^1$ is hydrogen, amino, hydroxy, or chloro; $R^3$ is hydrogen, or substituted or unsubstituted, saturated or unsaturated alkyl having from 1 to about 4 carbon atoms; wherein if $R^2$ is substituted, the substituent is one or more substituents selected from the group consisting of hydrogen, substituted and unsubstituted, saturated or unsaturated alkyl having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof.

3. The method according to claim 2, wherein $R^2$ is pyridine.

4. The method according to claim 2 wherein $R^2$ is pyrimidine.

5. The method according to claim 2 wherein $R^2$ is quaternary amine.

6. The method according to claim 2, wherein n=1.

7. The method according to claim 2, wherein n=2.

8. The method according to claim 2 wherein the reservoir is an oral composition comprising from about 0.002 mg to about 10 mg of a geminal bisphosphonic acid compound, or a pharmaceutically-acceptable salt or ester thereof, having the structure:

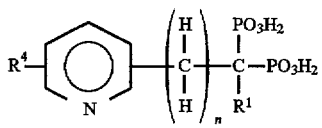

wherein n=1 or 2; $R^1$ is hydrogen, chloro, amino, or hydroxy; $R^4$ is one or more substituents selected from the group consisting of hydrogen, methyl, amino, chloro, methoxy, hydroxy, nitro, and combinations thereof; and the composition is a toothpaste, mouthwash, topical gel, or prophylaxis paste.

9. The method according to claim 8 wherein the bisphosphonic acid compound is 3-pyridyl-1-hydroxy-ethylidene-1,1-bisphosphonic acid or a pharmaceutically-acceptable salt or ester thereof.

10. The method according to claim 1 wherein the composition comprises a mobile ion concentration of a minimum of about 25% active compound ions.

11. The method according to claim 2 wherein the composition comprises a mobile ion concentration of a minimum of about 25% active compound ions.

12. The method according to claim 11 wherein the reservoir is a nonionic gel.

13. The method according to claim 1 wherein the reservoir comprises from about 0.01 mg to about 10 mg active compound.

14. The method according to claim 13 wherein the reservoir is an oral composition having a pH of from about 5 to about 9.

15. The method according to claim 14 wherein the amount of electrical current is from about 0.01 to about 1 ma/cm$^2$.

16. The method according to claim 14 wherein the amount of electrical current is from about 1 to about 5 ma/cm$^2$.

17. The method according to claim 14 wherein the electrical current is passed for from about 1 minute to about 2 hours.

18. The method of according to claim 17 wherein the frequency of treatment is form about once per three months to about 4 times per day.

19. The method according to claim 1 wherein the active compound of the reservoir composition is selected from the group consisting of 1-hydroxyethane-1,1-bisphosphonic acid; dichloromethane bisphosphonic acid; 3-amino-1-hydroxypropane-1,1-bisphosphonic acid; 6-amino-1-hydroxyhexane-1,1-bisphosphonic acid; 4-amino-1-hydroxybutane-1,1-bisphosphonic acid; 2-(3-pyridyl)-1-hydroxyethane-1,1-bisphosphonic acid; 2-(N-imidazoyl)-1-hydroxyethane-1,1-bisphosphonic acid; 3-(N-pentyl-N-methylamino)-1-hydroxypropane-1,1-bisphosphonic acid; 3-(N-pyrollidino)-1-hydroxypropane-1,1-bisphosphonic acid; N-cycloheptylaminomethanebisphosphonic acid; S-(p-chlorophenyl) thiomethanebisphosphonic acid; 4-amino-1-hydroxybutylidene-1,1-bisphosphonic acid; (7-dihydro-1-pyrindine)methane bisphosphonic acid; (7-dihydro-1-pyrindine)hydroxymethane bisphosphonic acid; (6-dihydro-2-pyrindine)hydroxymethanebisphosphonic acid; 2-(6-pyrolopyridine)-1-hydroxyethane-1,1-bisphosphonic acid; pharmaceutically-acceptable salts and esters of the above compounds, and mixtures thereof.

* * * * *